United States Patent [19]
Ortiz et al.

[11] Patent Number: 5,398,671
[45] Date of Patent: Mar. 21, 1995

[54] ABDOMINAL LIFT DEVICE
[75] Inventors: Mark S. Ortiz, Milford; Mark G. Steckel, Maineville, both of Ohio
[73] Assignee: Ethicon, Inc., Cincinnati, Ohio
[21] Appl. No.: 108,895
[22] Filed: Aug. 18, 1993
[51] Int. Cl.$^6$ ............................................. A61B 17/02
[52] U.S. Cl. ........................................ 128/20; 606/1
[58] Field of Search ............... 128/20, 3; 606/191, 606/198, 106.1; 604/104–106

[56] References Cited

U.S. PATENT DOCUMENTS

| | | | |
|---|---|---|---|
| 1,798,124 | 3/1931 | Hunn | 128/20 |
| 2,841,148 | 7/1958 | Kadavy | |
| 3,099,544 | 7/1963 | Sheesley | 101/491 |
| 3,831,587 | 8/1974 | Boyd | |
| 3,863,639 | 2/1975 | Kleaveland | |
| 3,888,117 | 6/1975 | Lewis | 128/20 X |
| 4,052,980 | 11/1977 | Grams et al. | |
| 4,151,838 | 5/1979 | Crew | |
| 4,232,660 | 11/1980 | Coles | |
| 4,291,687 | 9/1981 | Sinnreich | |
| 4,610,243 | 9/1986 | Ray | |
| 4,616,633 | 10/1986 | Vargas Garcia | |
| 4,616,634 | 10/1986 | Vargas Garcia | |
| 4,705,040 | 11/1987 | Mueller et al. | |
| 4,889,107 | 12/1989 | Kaufman | 128/20 |
| 4,945,897 | 8/1990 | Greenstein et al. | |
| 5,026,389 | 6/1991 | Thieler | 606/215 |
| 5,080,893 | 1/1992 | Goldberg et al. | 128/898 X |
| 5,152,086 | 2/1992 | Duh et al. | |
| 5,183,033 | 2/1993 | Wilk | |
| 5,183,465 | 2/1993 | Xanthakos et al. | |
| 5,308,327 | 5/1994 | Heaven et al. | 128/20 X |

FOREIGN PATENT DOCUMENTS

| | | |
|---|---|---|
| 0246086 | 5/1987 | European Pat. Off. |
| WO91/14392 | 10/1991 | WIPO |
| WO92/21291 | 12/1992 | WIPO |
| WO92/21292 | 12/1992 | WIPO |
| WO92/21293 | 12/1992 | WIPO |
| WO92/21294 | 12/1992 | WIPO |
| WO92/21295 | 12/1992 | WIPO |
| WO92/21298 | 12/1992 | WIPO |

OTHER PUBLICATIONS

Automated Medical Products Corp. brochure entitled "Iron Intern".
Kitano et al., "A Safe And Simple Method To Maintain A Clear Field Of Vision During Laparoscopic Cholecystectomy" from *Surgical Endoscopy* (1992) 6:197–198.
Hashimoto et al., "Laparoscopic Cholecysteomy: An Approach Without Pneumoperitoneum" from *Surgical Endoscopy* (1993) 7:54–56.
Akimaru et al., "Subcutaneous Wire Traction Technique With $CO_2$ Insufflation For Laparoscopic Cholecystectomy" from *Journal of Laparoendoscopic Surgery* (1993) 3: 59–62.
Automated Medical Products Corp. brochure entitled "Colon Resection".
Automated Medical Products Corp. brochure entitled "Abdominal Aortic Aneurysm".
Automated Medical Products Corp. brochure entitled "Anterior Colon Resection".
Automated Medical Products Corp. brochure entitled "Electrocoagulation Of Rectal Tumors".
Automated Medical Products Corp. brochure entitled "Kidney Transplants".
Automated Medical Products Corp. brochure entitled "Laparoscopic Surgery".
Automated Medical Products Corp. brochure entitled "Vaginal Hysterectomy".
Davis & Geck Endosurgery brochure entitled "Count On US".
Origin Medsystems, Inc. brochure Entitled "Gasless Laparoscopy".
Societe 3X brochure entitled "Le Pneumoperitoine En Suspension".
Societe 3X brochure entitled "Technical Notes Concerning The Suspender Of The Abdominal Wall".

*Primary Examiner*—Richard J. Apley
*Assistant Examiner*—Donna L. Maraglio
*Attorney, Agent, or Firm*—Dressler, Goldsmith, Shore & Milnamow, Ltd.

[57] ABSTRACT

An abdominal lift for use in endoscopic surgery is described. The lift defines a substantial portion of a circle. It has a spoke portion and an upstanding member. Its surface may be mechanically compliant and may be coated with an adhesion prevention agent or a lubricous coating. The described method of use includes use of a starter lift followed by insertion of the abdominal lift. The abdominal lift is elevated to establish a pneumoperitoneum at or near ambient air pressure.

15 Claims, 3 Drawing Sheets

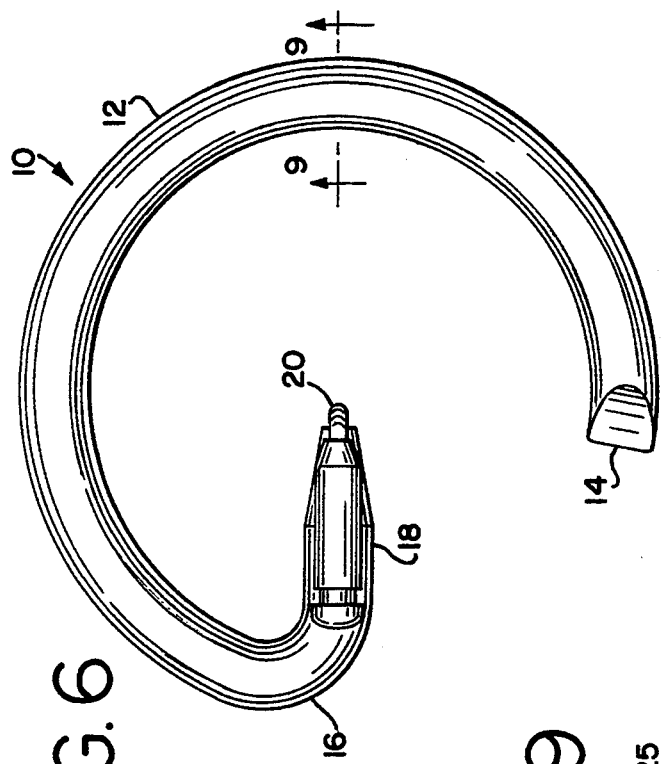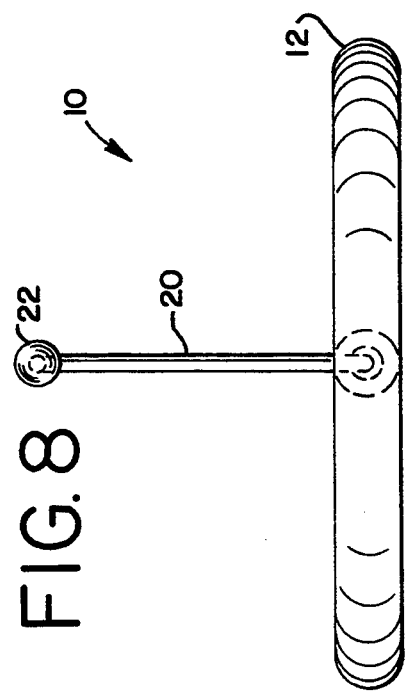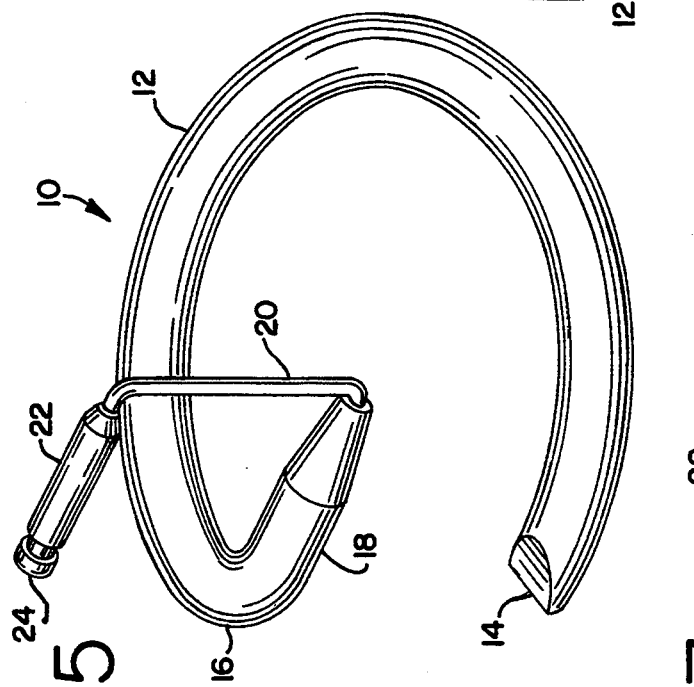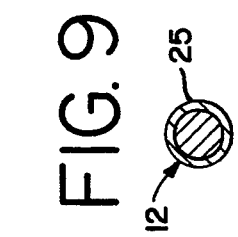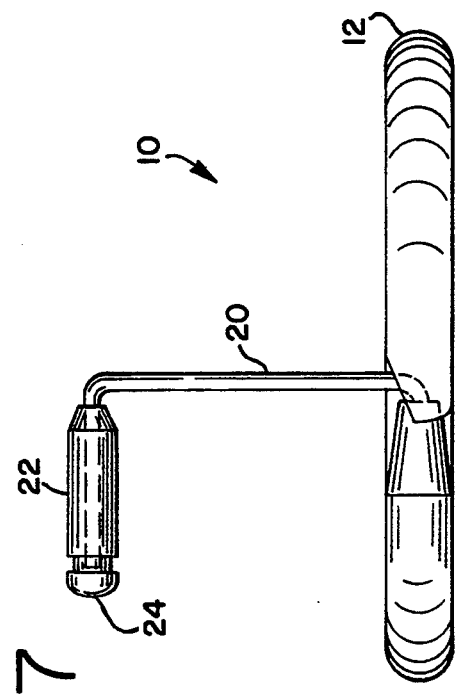

ABDOMINAL LIFT DEVICE

FIELD OF THE INVENTION

This invention relates generally to surgical instruments and, more particularly, to an abdominal lift device for use in laparoscopic surgery.

Background Of The Invention

Laparoscopic surgical procedures have been around for many years and up until recently have become more available due to advances in technology relating to the laparoscope or video imaging system. They are much less intrusive to the patient than typical open surgical procedures. While an open surgical procedure may involve one primary incision that is at least 6–9 centimeters long, a laparoscopic procedure typically uses smaller incisions, each only around 5–11 millimeters in length. In open surgery, the surgeon cuts muscle. In laparoscopic surgery, the surgeon generally does not cut muscle. Because they are less intrusive than open surgical procedures, laparoscopic procedures have resulted in much shorter surgical procedures and recovery times.

Laparoscopic procedures have typically involved insufflation of the abdominal or peritoneal cavity with carbon dioxide and/or other gases in order to create a pneumoperitoneum. The pneumoperitoneum establishes an open space inside the peritoneal cavity to enable the surgeon to move the laparoscope around and see inside.

Typically, the pneumoperitoneum is established by puncturing the abdominal wall with a Veress needle and injecting gas from an insufflator through the Veress needle into the peritoneal cavity to a pressure of around 12 mm Hg.

After insufflation, a trocar is advanced through the opening in the abdominal wall and into the peritoneal cavity. The trocar is a tube or cannula that usually has a gaseous seal to contain the carbon dioxide within the peritoneal cavity and maintain insufflation. The cannula is used for insertion of other medical instruments such as a laparoscope therethrough and into the peritoneal cavity.

There may be certain difficulties associated with insufflation of the peritoneal cavity. First and foremost is postoperative pain which patients may experience in the abdomen or shoulder area due to migrating gas. This occurs when insufflation causes excess gas pressure in the peritoneal cavity. Excess gas pressure may also compress the pleural cavities thus making respiration difficult. Other possible difficulties associated with insufflation in laparoscopic surgery include subcutaneous emphysema, blood vessel penetration, etc.

The attendant difficulties of insufflation have led to alternatives to insufflation wherein a pneumoperitoneum is established by elevating the abdominal wall with a mechanical lift. The lift is introduced percutaneously into the peritoneal cavity before establishing a pneumoperitoneum. The lift is elevated mechanically in order to distend the abdomen. When the abdomen is distended, ambient air enters the peritoneum through the puncture opening in the abdomen and a pneumoperitoneum at or near ambient air pressure is established.

By establishing a pneumoperitoneum at ambient air pressure, insufflation and the concomitant need for gaseous seals in endoscopic instruments and trocars for maintaining a relatively high gas pressure in the peritoneal cavity is eliminated. Thus, the attendant difficulties of insufflation, as well as the need for costly equipment, is eliminated.

The prior art includes several abdominal lift structures. Origin Medsystems, Inc. of Menlo Park, Calif. markets a lift under the trademark Laparofan TM. It has two radially extending blades that are rotatable. The blades are closed together for initial insertion into the abdominal cavity. After insertion, the blades are spread or fanned. When the lift is elevated, the blades contact and elevate the inner surface of the abdominal wall. Origin's device is described in International Patent Application PCT/US92/4456.

Societe 3X, a French company, markets an abdominal lift and support structure. The lift is shown and described in International Patent Application PCT/FR91/227. It contains a series of curves forming a generally triangular shape. The tip of the lift is turned downwardly slightly. The support structure has a crane and boom design. Gross adjustments are made by sliding the supporting leg and the boom within their respective holders. A mechanical screw-jack is used for fine adjustment.

International Patent Application PCT/FR91/227 describes an abdominal lift having various curves in different directions. U.S. Pat. No. 5,183,033 describes a method for lifting an abdominal wall with a set of linear and non-linear abdominal lifts. International Patent Application PCT/US92/4392 describes a variety of mechanical rods, arms and/or balloons for mechanically lifting an abdominal wall during laparoscopic surgery.

There are some other prior art structures for elevating and/or supporting abdominal lifts in laparoscopic surgery. U.S. Pat. No. 5,183,033 illustrates support structures using winches or U-shaped bars for use in laparoscopic surgery.

Further, there are a number of prior art support structures for supporting mechanical lifts used in open surgery. For example, see U.S. Pat. Nos. 5,109,831 and 4,143,652.

The ease of operation of these prior art lift devices without damage to internal viscera is limited. It would be desirable to provide an abdominal lift and a corresponding method of use with insertion into the peritoneal cavity without prior insufflation wherein the lift can be easily inserted and manipulated without creating adhesions, puncturing tissue, or otherwise pulling or damaging viscera. It would also be desirable to shed viscera that collects on the lift by manipulating the lift while it is inserted. It would also be desirable to provide a lift that has a substantially circular shape wherein it can be rotated while it is inserted with a minimum of resistance and a minimum of trauma to viscera. It would be desirable to provide an abdominal lift with an outer surface that minimizes friction and trauma to tissue.

SUMMARY OF THE INVENTION

The present invention is an abdominal lift having a curved portion that defines a substantial portion of a circle. A spoke portion extends radially inwardly from the curved portion and an upstanding member extends upwardly from the spoke portion. The upstanding member is connectable to a support structure which elevates and supports the abdominal lift. Preferably, the curved portion has a low coefficient of friction. In alternative embodiments, the curved portion has an outer layer that is mechanically compliant and/or has an adhesion prevention agent.

The method of use of the abdominal lift includes insertion of a starter lift into an opening in the abdominal wall and lifting the abdominal wall slightly. The abdominal lift is inserted into the opening and the starter lift is removed. The abdominal lift is rotated until it is fully inserted. Viscera is then shed from the abdominal lift by counter-rotating the lift. Finally, the abdominal lift is lifted in order to create an open space or pneumoperitoneum.

These and other aspects and attributes of the present invention will be discussed with reference to the following drawings and accompanying specification.

BRIEF DESCRIPTION OF THE DRAWINGS

FIG. 5 is a perspective view of the abdominal lift shown in FIG. 4;

FIG. 6 is a top view of the abdominal lift shown in FIG. 5;

FIG. 7 is an elevational view of the abdominal 10 lift shown in FIG. 5;

FIG. 8 is an elevational view of the abdominal lift shown in FIG. 7 with the lift rotated 90°; and FIG. 9 is a cross-sectional view taken along the line 9—9 in FIG. 6.

DETAILED DESCRIPTION OF THE DRAWINGS

Figure 1:
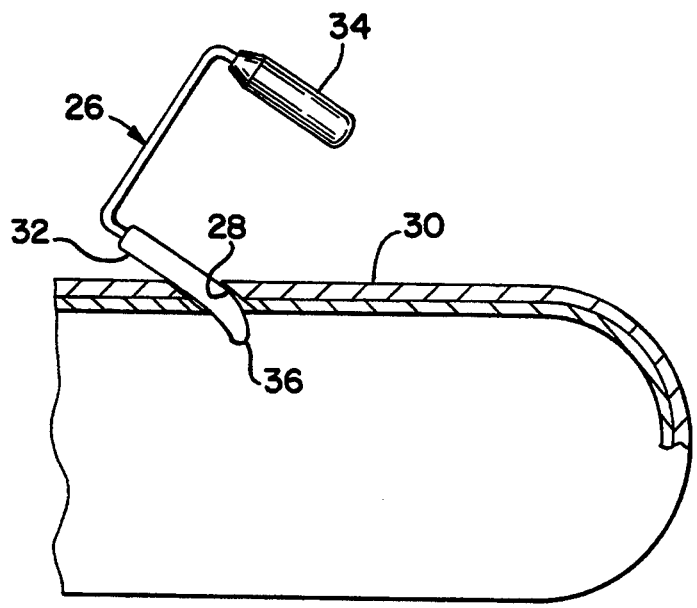
FIG. 1 is an elevational view of a starter lift being inserted into an opening in an abdominal wall (shown in cross-section)

While this invention is susceptible of embodiment in many forms, there is shown in the drawings, and will be described herein in detail, specific embodiments thereof with the understanding that the present disclosure is to be considered as an exemplification of the principles of the invention and is not intended to limit the invention to the specific embodiments illustrated.

Referring to FIGS. 5 and 6, an abdominal lift 10 in accordance with the invention includes a rigid curved lift portion 12 that defines a substantial portion of a circle. Preferably, the curved portion 12 extends around an approximately 270° arc. It has a tapered free end 14.

The closed end 16 of the curved portion 12 bends radially inwardly to form a rigid spoke portion 18. The spoke portion 18 extends inwardly to about the center of the circle where it is connected to a rigid upstanding member 20.

Referring to FIGS. 7 and 8, the upstanding member 20 extends vertically and terminates in a rigid handle member 22. The handle member 22 extends radially outwardly. The tip 24 of the handle member 22 has a fitting for connection to a cooperating support structure for elevating and supporting the lift. A support structure that is usable with the lift described herein is described in co-pending U.S. patent application Ser. No. 08/108,431, entitled Support Structure For Abdominal Lift, the disclosure of which application is incorporated by reference herein.

Preferably, the curved portion 12, as well as the spoke portion 18, upstanding member 20 and handle member 22, have a circular cross-section and have a smooth, rounded surface in order to minimize tissue trauma. In a preferred embodiment, they are formed of a solid plastic or metal suitable for surgical use.

The outer surface of the curved portion 12 and spoke member 18 are preferably formed of a layer 25 (FIG. 9) of mechanically compliant material to further minimize tissue trauma. Preferably, the mechanically compliant material is an open or closed cell polymeric foam, an elastomeric material of low durometer, or a soft textile material such as fiber felt. The foam material may be formed of any of a variety of materials suitable for surgical use, including polyethylene, polyurethane, cellulose, oxidized cellulose, collagen or nylon. Alternatively, the compliant material may be an elastomeric material of low durometer (less than 90 Shore A), such as silicone, polyurethane or polyetheramide. A felt compliant material can be made from fibers of oxidized cellulose, polyester, nylon, etc.

The outer surface may hold or be coated with an adhesion prevention agent such as hyaluronic acid or a derivative of it. Alternatively, the outer surface may have a highly lubricous coating. For example, the lubricous coating may be a hydrophilic material known as hydrogel which is based on a polymer such as PVP, PEG, POLYHEMA, or polyacrylamide. Preferably, a smooth outer surface having a coefficient of friction of less than 0.1 is maintained. The coating may be used in combination with a mechanically compliant outer layer 25 as described above.

In a method of use in accordance with the invention, a starter lift 26 is introduced into an opening 28 in the abdominal wall 30, as shown in FIG. 1. The starter lift 26 includes a lift portion 32 and a handle 34. Preferably, the lift portion 32 has a smooth, rounded outer surface to minimize tissue trauma. The tip 36 may be angled downward slightly in order to facilitate ease of entry into an abdominal opening 28. As the starter lift 26 is inserted into the opening 28, the abdominal wall 30 is raised slightly and the starter lift 26 fits under it.

Figure 2:
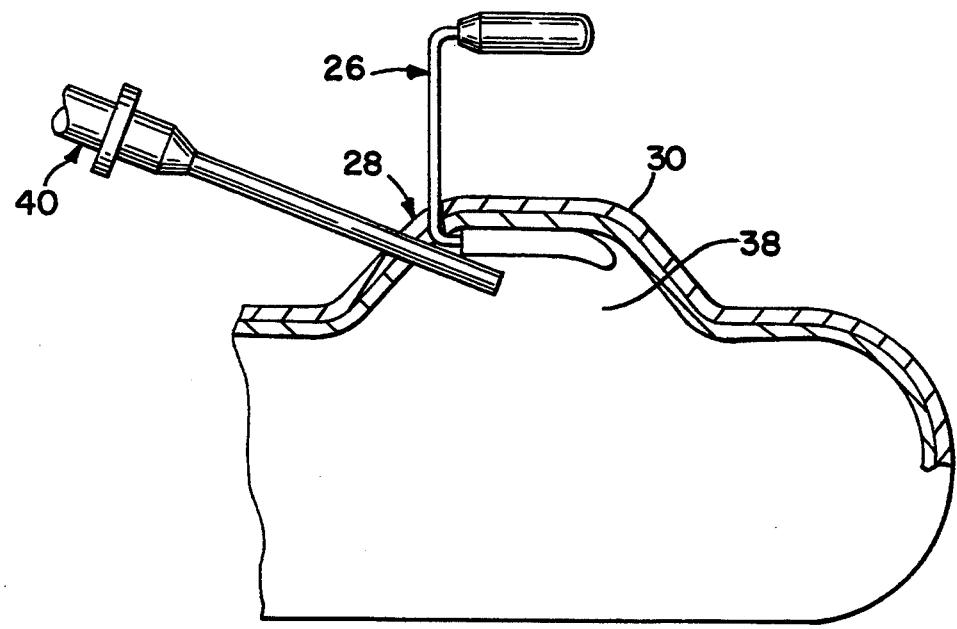
FIG. 2 is a view of the starter lift shown in FIG. 1 wherein the starter lift is elevated slightly and a laparoscope is inserted into the opening.

Referring to FIG. 2, when the starter lift 26 is fully inserted into the opening 28, it is raised in order to raise the abdominal wall 30 and create a pneumoperitoneum 38. A laparoscope 40 may be inserted through the opening 28 in order to preliminary view internal organs. The laparoscope is removed before insertion of the abdominal lift 10.

Figure 3:
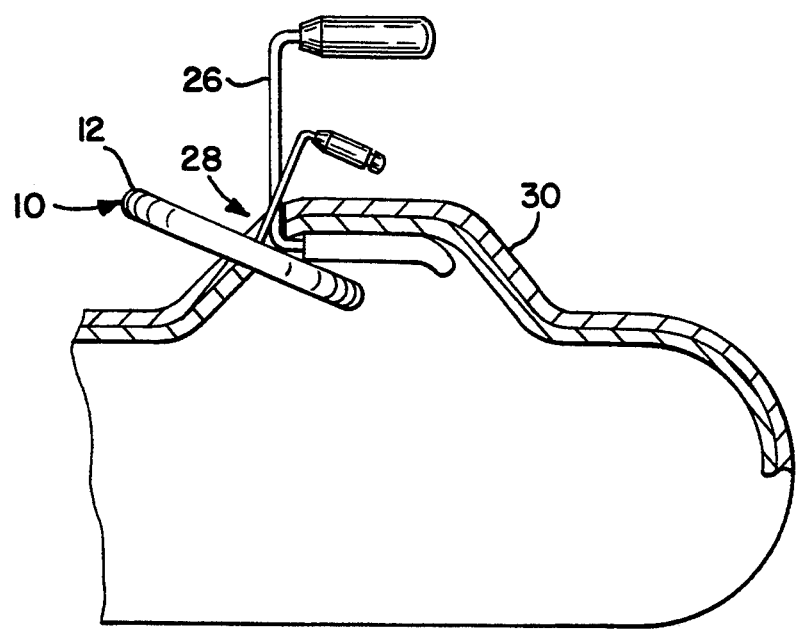
FIG. 3 is a view of the starter lift and abdominal wall as shown in FIG. 2 wherein an abdominal lift in accordance with the invention is partially inserted into the opening.

Referring to FIG. 3, the abdominal lift 10 is inserted into the opening 28 while the starter lift 26 and abdominal wall 30 are raised slightly. The starter lift 26 is removed and the abdominal lift 10 is then fully inserted. As the curved portion 12 of abdominal lift 10 is inserted in the opening 28, it is preferably rotated in a clockwise direction when viewed from above (as shown in FIG. 6). After the curved portion 12 is inserted, then the spoke portion 18 is inserted until the upstanding member 20 is positioned directly over the opening 28. At this point, the abdominal lift 10 may be counter-rotated in a counter-clockwise direction to shed internal viscera that may have collected on the lift 10.

Figure 4:
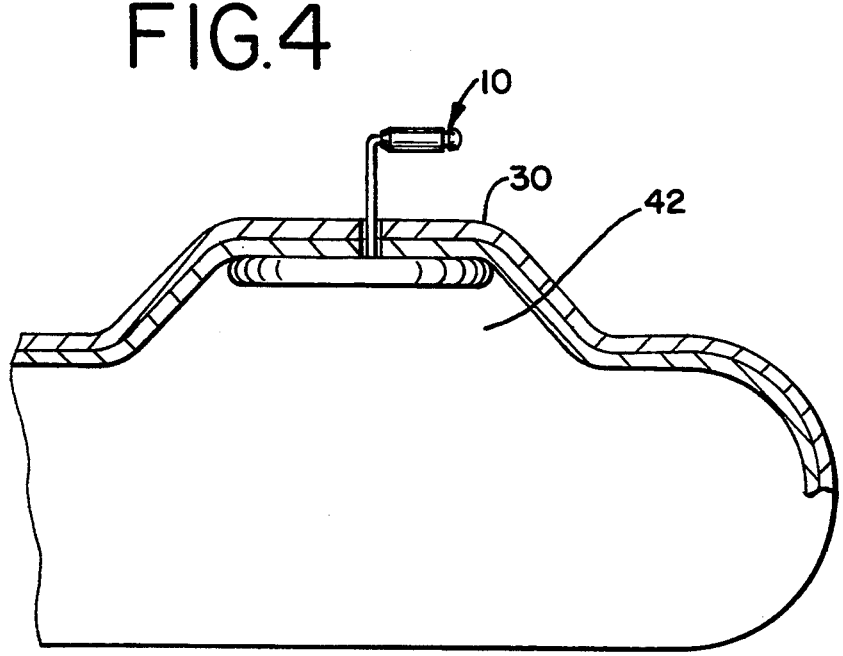
FIG. 4 is an elevational view of an abdominal lift in accordance with the invention that is fully inserted through an opening in the abdominal wall (shown in cross-section)

Referring to FIG. 4, the abdominal lift 10 is connected to a support structure (not illustrated) for supporting an abdominal lift and the lift 10 is raised to create a pneumoperitoneum 42 for use in endoscopic surgery. The lift force is preferably in the range of 6 lbs. to 10 lbs.

From the foregoing, it will be observed that numerous modifications and variations can be effected without departing from the true spirit and scope of the novel concept of the present invention. It is to be understood that no limitation with respect to the specific embodiment is intended or should be inferred. The disclosure is intended to cover by the appended claims all such modifications as fall within the scope of the claims.

What is claimed:

1. An abdominal lift device, comprising:
   a rigid curved lift portion, said lift portion having substantially the same radius of curvature continuously along the length thereof so as to define a substantial portion of a circle having a tapered free end and a closed end;
   a spoke portion extending radially inwardly from said closed end of said lift portion;
   an upstanding member extending from said spoke portion and having a lower end connected to said spoke portion, said lower end of said upstanding member being located substantially in the center of said lift portion; and
   a handle member extending from said upstanding member, said handle member lying in a plane substantially parallel to said lift portion.

2. An abdominal lift device in accordance with claim 1 wherein said upstanding member is substantially vertical.

3. An abdominal lift device in accordance with claim 1 wherein said curved portion extends approximately 270°.

4. An abdominal lift device in accordance with claim 1 wherein said curved lift portion includes a mechanically compliant outer layer.

5. An abdominal lift device in accordance with claim 1 wherein said spoke portion includes a mechanically compliant outer layer.

6. An abdominal lift device in accordance with claim 4 wherein said mechanically compliant outer layer comprises an open cell polymeric foam.

7. An abdominal lift device in accordance with claim 4 where said mechanically compliant outer layer comprises a closed cell polymeric foam.

8. An abdominal lift device in accordance with claim 4 wherein said mechanically compliant outer layer comprises a soft textile material.

9. An abdominal lift device in accordance with claim 4 wherein said mechanically compliant outer layer comprises an elastomeric material of low durometer.

10. An abdominal lift device in accordance with claim 1 wherein said curved lift portion includes an adhesion prevention agent.

11. An abdominal lift device in accordance with claim 10 wherein said adhesion prevention agent comprises hyaluronic acid.

12. An abdominal lift device in accordance with claim 10 wherein said adhesion prevention agent comprises a derivative of hyaluronic acid.

13. An abdominal lift device in accordance with claim 1 wherein said spoke portion includes an adhesion prevention agent.

14. An abdominal lift device in accordance with claim 1 wherein said curved lift portion has a coefficient of friction below approximately 0.1.

15. An abdominal lift device in accordance with claim 1 wherein said spoke portion has a coefficient of friction below approximately 0.1.

* * * * *